United States Patent
Joye et al.

(10) Patent No.: US 6,908,462 B2
(45) Date of Patent: Jun. 21, 2005

(54) APPARATUS AND METHOD FOR CRYOGENIC INHIBITION OF HYPERPLASIA

(75) Inventors: James Joye, Los Gatos, CA (US); Ronald Williams, Menlo Park, CA (US)

(73) Assignee: CryoVascular Systems, Inc., Los Gatos, CA (US)

( * ) Notice: Subject to any disclaimer, the term of this patent is extended or adjusted under 35 U.S.C. 154(b) by 178 days.

(21) Appl. No.: 09/978,253

(22) Filed: Oct. 15, 2001

(65) Prior Publication Data

US 2002/0026182 A1 Feb. 28, 2002

Related U.S. Application Data

(60) Division of application No. 09/203,011, filed on Dec. 1, 1998, now Pat. No. 6,355,029, which is a continuation-in-part of application No. 08/982,824, filed on Dec. 2, 1997, now Pat. No. 5,971,979.

(51) Int. Cl.$^7$ .............................................. A61B 18/18
(52) U.S. Cl. ............................ 606/20; 606/21; 606/22; 128/898
(58) Field of Search ..................... 606/20–26; 607/105; 128/898; 604/96.01, 104

(56) References Cited

U.S. PATENT DOCUMENTS

| | | |
|---|---|---|
| 3,901,241 A | 8/1975 | Allen, Jr. |
| 4,336,691 A | 6/1982 | Burstein et al. |
| 4,754,752 A | 7/1988 | Ginsburg et al. |
| 5,019,075 A | 5/1991 | Spears et al. |
| 5,041,089 A | 8/1991 | Mueller et al. |
| 5,078,713 A | 1/1992 | Varney |
| 5,092,841 A | 3/1992 | Spears |
| 5,106,360 A | 4/1992 | Ishiwara et al. |
| 5,147,355 A | 9/1992 | Friedman et al. |
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,275,595 A | 1/1994 | Dobak, III |
| 5,458,612 A | 10/1995 | Chin |
| 5,486,208 A | 1/1996 | Ginsburg |
| 5,501,681 A | 3/1996 | Neuwirth et al. |

(Continued)

FOREIGN PATENT DOCUMENTS

| | | |
|---|---|---|
| WO | WO 91/05528 | 2/1991 |
| WO | WO 98/38934 A1 | 3/1998 |
| WO | WO 98/49957 | 11/1998 |
| WO | WO 01/64145 | 9/2001 |

OTHER PUBLICATIONS

Examination Report (Registered Letter) from European Patent Office dated Mar. 18, 2004, for Application No. 98 959 646.5—2305 under the name Odyssey Technologies, Inc. (6 pgs).

Gage, M.D., Andrew A., et al., "Freezing injury to large blood vessels in dogs," Surgery, vol. 61, No. 5, May, 1997, pp. 748–754.

*Primary Examiner*—Rosiland Rollins
(74) *Attorney, Agent, or Firm*—Townsend & Townsend & Crew LLP; Mark D. Barrish

(57) ABSTRACT

Post-angioplasty hyperplasia in blood vessels is treated using a cryosurgical balloon catheter. The balloon catheter is positioned at a target region within the blood vessel, and the balloon inflated by expanding a cryogenic fluid, such as liquid nitrogen, across an expansion orifice into a balloon. The balloon will be constructed so that cooling is achieved primarily in the central regions of the balloon, with the proximal and distal regions being less cold and acting to insulate adjacent regions of the blood vessel from excessive cooling.

11 Claims, 7 Drawing Sheets

U.S. PATENT DOCUMENTS

| | | |
|---|---|---|
| 5,520,682 A | 5/1996 | Baust et al. |
| 5,545,195 A | 8/1996 | Lennox et al. |
| 5,617,739 A | 4/1997 | Little |
| 5,644,502 A | 7/1997 | Little |
| 5,733,280 A | 3/1998 | Avitall |
| 5,868,735 A | 2/1999 | Lafontaine |
| 6,235,019 B1 * | 5/2001 | Lehmann et al. .............. 606/22 |
| 6,241,718 B1 | 6/2001 | Arless et al. |
| 6,283,959 B1 * | 9/2001 | Lalonde et al. ............... 606/21 |
| 6,290,696 B1 | 9/2001 | Lafontaine |
| 6,624,392 B2 | 9/2003 | Li |

* cited by examiner

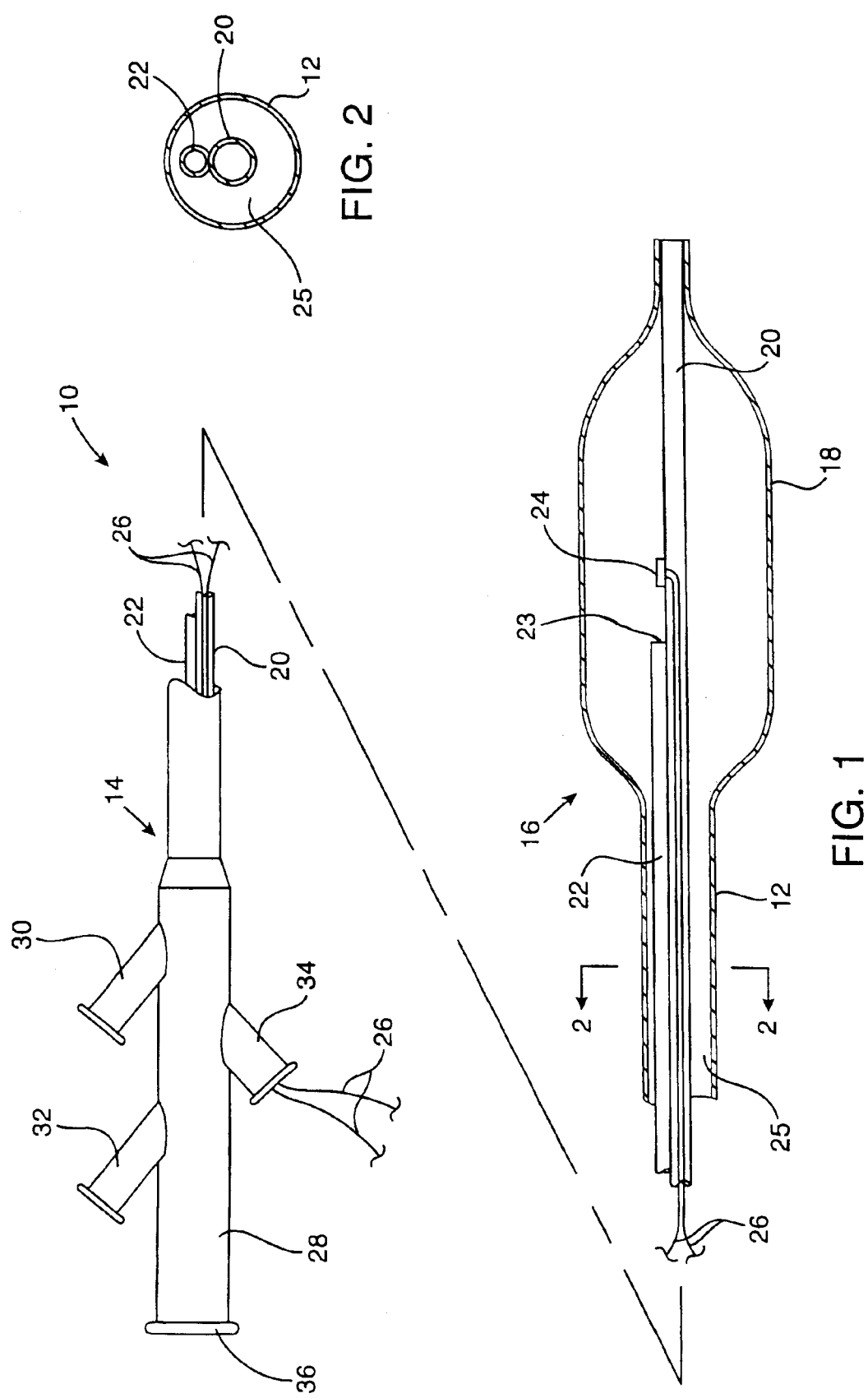

APPARATUS AND METHOD FOR CRYOGENIC INHIBITION OF HYPERPLASIA

CROSS-REFERENCES TO RELATED APPLICATIONS

This application is a divisional of, and claims priority from U.S. patent application Ser. No. 09/203,011 filed Dec. 1, 1998 now U.S Pat. No. 6,355,029, which is a continuation-in-part of, and claims the benefit of priority from, U.S. patent application Ser. No. 08/982,824, filed Dec. 2, 1997 now U.S. Pat. No. 5,971,979, the full disclosures of which are incorporated herein by reference.

BACKGROUND OF THE INVENTION

1. Field of the Invention

The present invention relates generally to apparatus and methods for inhibiting restenosis in arteries following angioplasty or other intravascular procedures for treating atherosclerotic disease. More particularly, the present invention relates to apparatus and methods for cryogenically treating the target site within a patient's vasculature to inhibit hyperplasia which can occur after such intravascular procedures.

A number of percutaneous intravascular procedures have been developed for treating atherosclerotic disease in a patient's vasculature. The most successful of these treatments is percutaneous transluminal angioplasty (PTA) which employs a catheter having an expansible distal end, usually in the form of an inflatable balloon, to dilate a stenotic region in the vasculature to restore adequate blood flow beyond the stenosis. Other procedures for opening stenotic regions include directional arthrectomy, rotational arthrectomy, laser angioplasty, stents and the like. While these procedures, particularly PTA, have gained wide acceptance, they continue to suffer from the subsequent occurrence of restenosis.

Restenosis refers to the re-narrowing of an artery within weeks or months following an initially successful angioplasty or other primary treatment. Restenosis afflicts up to 50% of all angioplasty patients and results at least in part from smooth muscle cell proliferation in response to the injury caused by the primary treatment, generally referred to as "hyperplasia." Blood vessels in which significant restenosis occur will require further treatment.

A number of strategies have been proposed to treat hyperplasia and reduce restenosis. Such strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While enjoying different levels of success, no one of these procedures has proven to be entirely successful in treating all occurrences of restenosis and hyperplasia.

For these reasons, it would be desirable to provide additional apparatus and methods suitable for the treatment of restenosis and hyperplasia in blood vessels. It would be further desirable if the apparatus and methods were suitable for treatment of other conditions related to excessive cell proliferation, including neoplasms resulting from tumor growth, hyperplasia in other body lumens, and the like. The apparatus and method should be suitable for intravascular and intraluminal introduction, preferably via percutaneous access. It would be particularly desirable if the methods and apparatus were able to deliver the treatment in a very focused and specific manner with minimal effect on adjacent tissues. Such apparatus and methods should further be effective in inhibiting hyperplasia and/or neoplasia in the target tissue with minimum side affects. At least some of these objectives will be met by the invention described hereinafter.

2. Description of the Background Art

Balloon catheters for intravascularly cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691.

The full disclosures of each of the above U.S. patents are incorporated herein by reference.

SUMMARY OF THE INVENTION

The present invention comprises the cryosurgical treatment of a target site within the body lumen of a patient, usually in an artery which has been previously treated for atherosclerotic disease by balloon angioplasty or any of the other primary treatment modalities described above. The present invention, however, is further suitable for treating other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Inhibition of such excessive cell growth is necessary to maintain patency of the lumen.

Treatment according to the present invention is effected by cooling target tissue to a temperature which is sufficiently low for a time which is sufficiently long to inhibit excessive cell proliferation. The cooling treatment will be directed against all or a portion of a circumferential surface of the body lumen, and will preferably result in cell growth inhibition, but not necessarily in significant cell necrosis. Particularly in the treatment of arteries following balloon angioplasty, cell necrosis may be undesirable if it increases the hyperplastic response. Thus, the present invention will slow or stop cell proliferation but may leave the cells which line the body lumen viable, thus lessening hyperplasia.

Methods according to the present invention comprise cooling an inner surface of the body lumen to a temperature and for a time sufficient to inhibit subsequent cell growth. Generally, the temperature at the tissue surface will be in a range from about 0° C. to about −80° C., the tissue surface temperature preferably being in a range from about −10° C. to about −40° C. In other embodiments, the temperature at the cell surface can be in the range from −20° C. to −80° C., optionally being from −30° C. to −50° C. The tissue is typically maintained at the described temperature for a time period in the range from about 1 to about 60 seconds, often being from 1 second to 10 seconds, preferably from 2 seconds to 5 seconds. Hyperplasia inhibiting efficacy may be enhanced by repeating cooling in cycles, typically with from about 1 to 5 cycles, with the cycles being repeated at a rate of about one cycle every 60 seconds. In the case of arteries, the cooling treatment will usually be effected very shortly after angioplasty, arthrectomy, rotational arthrectomy, laser angioplasty, stenting, or another primary treatment procedure, preferably within one hour of the primary treatment, more preferably within thirty minutes within the primary treatment, and most preferably immediately following the primary treatment.

The methods of the present invention may be performed with cryosurgical catheters comprising a catheter body having a proximal end, a distal end, and a primary lumen therethrough. The primary lumen terminates in a Joule-Thomson orifice at or near its distal end, and a balloon is disposed over the orifice on the catheter body to contain a cryogenic fluid delivered through the primary lumen. Suitable cryogenic fluids will be non-toxic and include liquid nitrogen, liquid nitrous oxide, liquid carbon dioxide, and the like. By delivering the cryogenic fluid through the catheter body, the balloon can be expanded and cooled in order to effect treatments according to the present invention.

Preferably, the Joule-Thomson orifice will be spaced inwardly from each end of the balloon and the balloon will be sufficiently long so that the cooling of the balloon occurs primarily in the middle. The temperature of the proximal and distal ends of the balloon will thus be much less than that of the middle, and the ends will thus act as "insulating" regions which protect luminal surfaces and other body structures from unintended cooling. Preferably, the balloon has a length of at least 1 cm, more preferably at least 2 cm, and typically in the range from 3 cm to 10 cm. The orifice is usually positioned at least 0.5 cm from each end, preferably being at least 1 cm from each end in balloons which are 2 cm or longer.

While it has been found that positioning of the Joule-Thomson valve in the central region of a balloon will usually provide sufficient insulation of each end resulting from the inherent heat transfer characteristics, in some instances it will be desirable to provide a separate containment bladder nested inside the balloon to receive the cryogenic fluid. The containment bladder will further act to limit cooling to the central region of the balloon. The portions of the balloon proximal and distal to the containment bladder may optionally be inflated with an insulating medium, such as a gas, silicone oil, saline, or the like. Alternatively, the containment bladder may have a vent or be partially porous so that the cryogenic fluid (which is present as a gas within the containment bladder) flows at a controlled rate into the overlying balloon. By limiting the flow rate, the temperature of the cryogenic fluid will be significantly higher in the regions outside of the containment bladder but still within the balloon.

In another aspect, the present invention provides a cryosurgical system comprising a flexible catheter body having a proximal end, a distal end, and a gas exhaust lumen defining an axis therebetween. An intravascular balloon is disposed near the distal end of the catheter body in fluid communication with the exhaust lumen. The balloon is expandable to radially engage a surrounding vessel wall. A cryogenic cooling fluid supply is in fluid communication with at least one port disposed within the balloon.

As described above, the at least one port may optionally comprise a Joule Thompson orifice. Alternatively, the at least one port may pass some or all of the cryogenic cooling fluid as a liquid. In fact, a plurality of ports may spray the fluid radially, the liquid in some cases distributed substantially uniformly over an inner surface of the balloon wall so that enthalpy of vaporization of the liquid cools a region of the balloon wall. The vaporization of the liquid will help to inflate the balloon, while the exhaust lumen limits pressure within the balloon to safe levels.

In another aspect, the invention provides a cryosurgical catheter for use in a blood vessel having a vessel wall. The cryosurgical catheter comprises a flexible catheter body having a proximal end, a distal end, and a gas exhaust lumen defining an axis therebetween. A balloon is disposed at the distal end of the catheter body in fluid communication with the exhaust lumen. The balloon has a balloon wall with proximal and distal ends and a radially oriented region extending therebetween. The wall is radially expandable to engage the surrounding vessel wall. At least one cooling fluid distribution port is in communication with a cryogenic cooling fluid supply. The at least one port is disposed within the balloon to cool the region of the expanded balloon wall.

The cryosurgical methods and catheters of the present invention will often be tailored to provide even cooling along at least a portion of a vascular wall engaged by the cooled balloon. For example, the efficacy of cryogenic cell growth inhibition may be enhanced significantly by distributing cooling within the balloon using a plurality of cryogenic fluid ports distributed circumferentially and/or axially within the balloon so that a significant portion of the vessel wall engaging the balloon surface is cooled to the target temperature range for a time in the desired treatment period range.

In this aspect, the present invention provides a cryosurgical catheter for use in a blood vessel having a vessel wall. The cryosurgical catheter comprises a flexible catheter body having a proximal end, a distal end, and a lumen defining an axis therebetween. A balloon is disposed at the distal end of the catheter body. The balloon is in fluid communication with the lumen, and has a balloon wall that expands radially to engage the surrounding vessel wall. A plurality of cooling fluid distribution ports are in communication with a cooling fluid supply. These ports are distributed within the balloon so as to evenly cool a portion of the vessel wall.

To maximize cooling efficiency and minimize gas pressure within the balloon, it is generally preferable to minimize the total cooling fluid flow out of the exhaust lumen from the balloon. Efficiency can also be enhanced by directing the cooling fluid radially against the balloon wall, ideally using a plurality of ports that are separated circumferentially about a diffuser head. When treating long diseased segments of the vasculature, for example, when treating hyperplasia of the iliac or superior femoral arteries, it would be beneficial to treat the entire segment without moving or repositioning the balloon. To provide even treatment within such an elongated diseased vessel, the diffuser head may be moved axially within the inflated balloon by sliding a cooling fluid supply tube axially within the catheter body. Such a structure may provide a variety of controllable sequential cryogenic treatment regimens, for example, multiple temperature feedback controlled cryogenic treatment cycles for inhibiting cell proliferation, or for a variety of alternative endoluminal cryogenic therapies. Alternatively, a fixed diffuser head defining an axially and circumferential distributed array of ports may provide simultaneous even cooling throughout a significant region of the target site.

In a related method aspect, the invention provides a therapy for treatment of a blood vessel having a vessel wall. The method comprises introducing a catheter into the blood vessel, and expanding a balloon of the catheter near a target site to engage the vessel wall. Fluid is expanded at a first location within the balloon. Fluid is also expanded at a second location within the balloon to cryogenically cool a portion of the engaged vessel wall, the second location being separated from the first location.

Gas expansion may effect cryogenic cooling via Joule-Thompson expansion as the cryogenic fluid enters the balloon and/or via the enthalpy of vaporization of a cryogenic fluid within the balloon. There may be significant temperature transients when cryogenic cooling is first initiated from within the balloon catheter. To enhance the surgeon's control over the cooling rate and treatment time of these cryogenic therapies, gas expansion may be initiated while a moveable orifice head is disposed within a housing or shield at one end of the balloon. This housing may conveniently be formed by extending a tubular structure distally from the catheter body into the interior of the balloon. Such a housing structure may also be used to help direct exhaust gases proximally out of the balloon without causing excessive cooling at the proximal end of the balloon, which exhaust gases might otherwise freeze blood within the vessel.

In yet another aspect, the invention also provides a kit for treating hyperplasia or neoplasia in a body lumen. The kit comprises a catheter having a proximal end, a distal end, and balloon near its distal end. Instructions are included in the kit for use of the catheter. These instructions comprise the step of cooling an inner surface of the body lumen with the balloon to a temperature and for a time sufficient to inhibit subsequent cell growth. Such a kit may include instructions for any of the methods described herein.

BRIEF DESCRIPTION OF THE DRAWINGS

FIG. 1 illustrates a cryosurgical catheter constructed in accordance with the principles of the present invention, with a distal end shown in cross-section.

FIG. 2 is a cross-sectional view of the catheter taken along line 2—2 in FIG. 1.

DESCRIPTION OF THE SPECIFIC EMBODIMENTS

Figure 4:
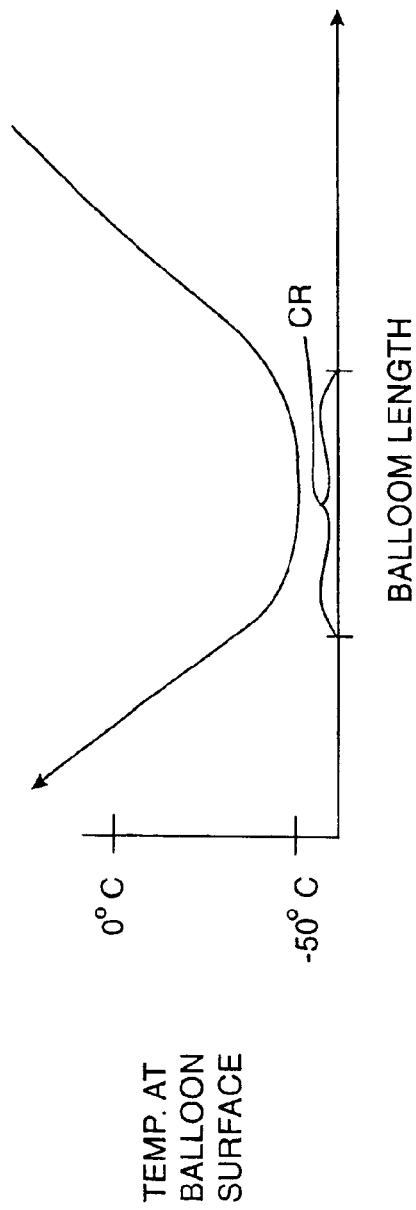
FIG. 4 is a graph illustrating the temperature profile of the balloon of FIGS. 1 and 3 while liquid nitrogen is being expanded therein and the balloon is present in a body lumen.

An exemplary cryosurgical catheter 10 constructed in accordance with the principles of the present invention is illustrated in FIGS. 1 and 2. The catheter 10 comprises a catheter body 12 having a proximal end 14, a distal end 16, and an inflatable balloon 18 disposed at the distal end. The balloon 18 is shown to be an integral extension of the catheter body 12, but such a structure is not required by the present invention. The balloon could be formed from the same or a different material and, in the latter case, attached to the distal end of the catheter body 12 by suitable adhesives, heat welding, or the like. The catheter body may be formed from conventional materials, such as polyethylenes, polyimides, and copolymers and derivatives thereof. The balloon may also be formed from conventional materials used for angioplasty balloons, typically being non-distensible, such as polyethylene terephthalate (PET).

Catheter 10 comprises a central shaft 20 which may be formed from polymeric material, such as polyethylene, polytetrafluoroethylene, polyimide, or from a metal, such as from hypotube. In the embodiment of catheter 10, the coaxial shaft 20 is tubular and provides a guidewire lumen for positioning of the catheter over a guidewire in a conventional manner. The shaft 20, however, could have a variety of other configurations and purposes. For example, the shaft could be a solid wire or core and further optionally provide a guidewire tip at its distal end. The shaft could also provide a lumen for delivering cryogenic fluid to the balloon 18. In the illustrated embodiment of FIG. 10, however, the cryogenic fluid is provided by a separate cryogenic fluid delivery tube 22 which is disposed in parallel to the coaxial shaft 20.

The catheter 10 will usually further comprise a thermocouple 24 which is optimally located near the center of balloon 18. At this location, it can measure the temperature of the cryogenic fluid after expansion from the proximal end of the cryogenic delivery tube 22. The cryogenic delivery tube 22 will define an expansion orifice at its distal end 23. Thus, the cryogenic fluid will flow through the tube 22 as a liquid at an elevated pressure and (thus inhibiting flow restrictive film boiling) will expand across the orifice 23 to a gaseous state at a lower pressure within the balloon. For liquid nitrogen, the pressure within the tube 22 will typically be in the range from 50 psi to 500 psi at a temperature below the associated boiling point. After expansion, the nitrogen gas within the balloon near its center (the location of thermocouple 24) the pressure will typically be in the range from 30 psi to 100 psi and the temperature in the range from −40° C. to −100° C. The temperature may decrease in both the radially outward direction and in both axial directions from the center of the balloon. This feature of the present invention is better described in connection with FIGS. 3 and 4 below.

A hub 28 is secured to the proximal end 14 of the catheter body 12. The hub provides for a port 30 for connecting a cryogenic fluid source to the cryogenic delivery tube 22. The hub further provides a port 32 for exhausting the gaseous cryogenic fluid which travels from balloon 18 in a proximal direction through annular lumen 25. A third port 34 is provided for thermocouple wires 26. A fourth port 36 at the proximal end of the hub is provided for a guidewire.

Figure 3:
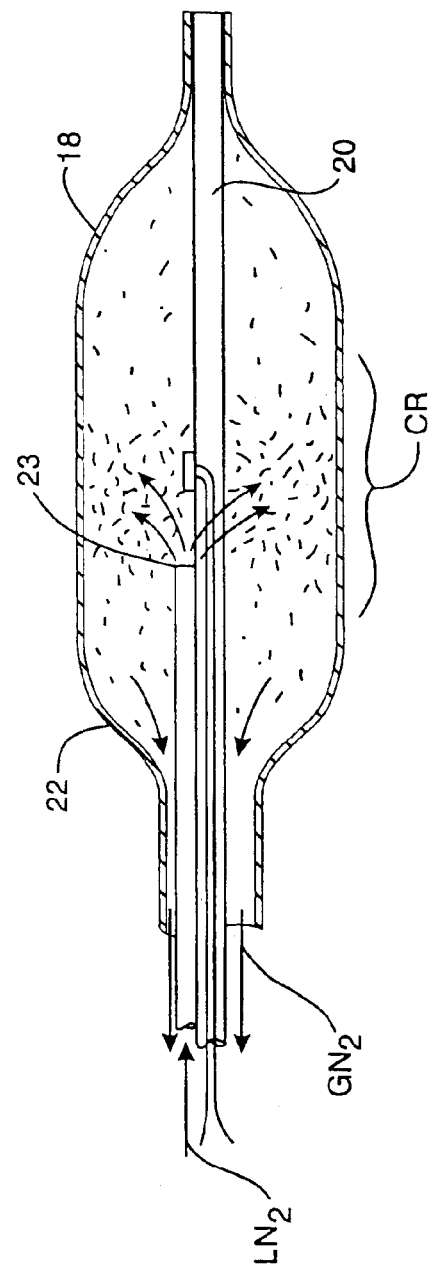
FIG. 3 illustrates the expansion of a cryogenic fluid within the balloon of the cryosurgical catheter of FIG. 1.

Referring now to FIGS. 3 and 4, liquid nitrogen (LN2) is delivered to balloon 18 through the cryogenic delivery tube 22. The liquid nitrogen is delivered at a temperature and pressure within in the ranges set forth above and expands to gaseous nitrogen (GN2) across the expansion orifice into the interior of balloon 18. In the single-balloon embodiment catheter 10, the gaseous nitrogen will serve both to inflate the balloon 18 and to cool the exterior surface of the balloon in a desired temperature profile. In particular, the balloon dimensions and operating conditions will be selected to provide a particular balloon temperature profile, an example of which is set forth in FIG. 4. By expanding the liquid nitrogen to its gaseous state near the center of the balloon, the balloon temperature will be lowest near the center and will decrease in both axial directions away from the center, as shown in the temperature profile of FIG. 4.

For treating arterial hyperplasia, a balloon temperature in the range from −20° C. to −80° C., e.g., at about −50° C., for a time period in the range from 1 second to 10 seconds, may be effective. By delivering the liquid nitrogen at a pressure in the range from 50 psi to 500 psi and at a temperature below the boiling point, and expanding the liquid nitrogen to a gas at a pressure in the range from 30 psi to 100 psi, a temperature in the above range at the middle of the balloon will be achieved. Moreover, by extending the balloon by distances of at least 0.5 cm, preferably of at least 1 cm, in each direction from the center of the balloon, the temperatures at the ends of the balloons will generally no lower than 0° C. In this way, a desired low temperature can be maintained at the outer surface of the balloon in a treatment region near the center of the balloon, while the distal and proximal ends of the balloon act to insulate the colder portions from non-target regions within the artery or other body lumen. It will be appreciated that the axial length of the treatment region of the balloon can be varied considerably by varying the length of the balloon and controlling the volume of liquid nitrogen delivered to the balloon. Exemplary balloons will have a length in the range from 3 cm to 5 cm, a diameter in the range from 1.5 mm to 4 mm, and will typically receive from 0.08 ml/sec to 1.5 ml/sec of liquid nitrogen in the temperature and pressure ranges set forth above.

Figure 5:
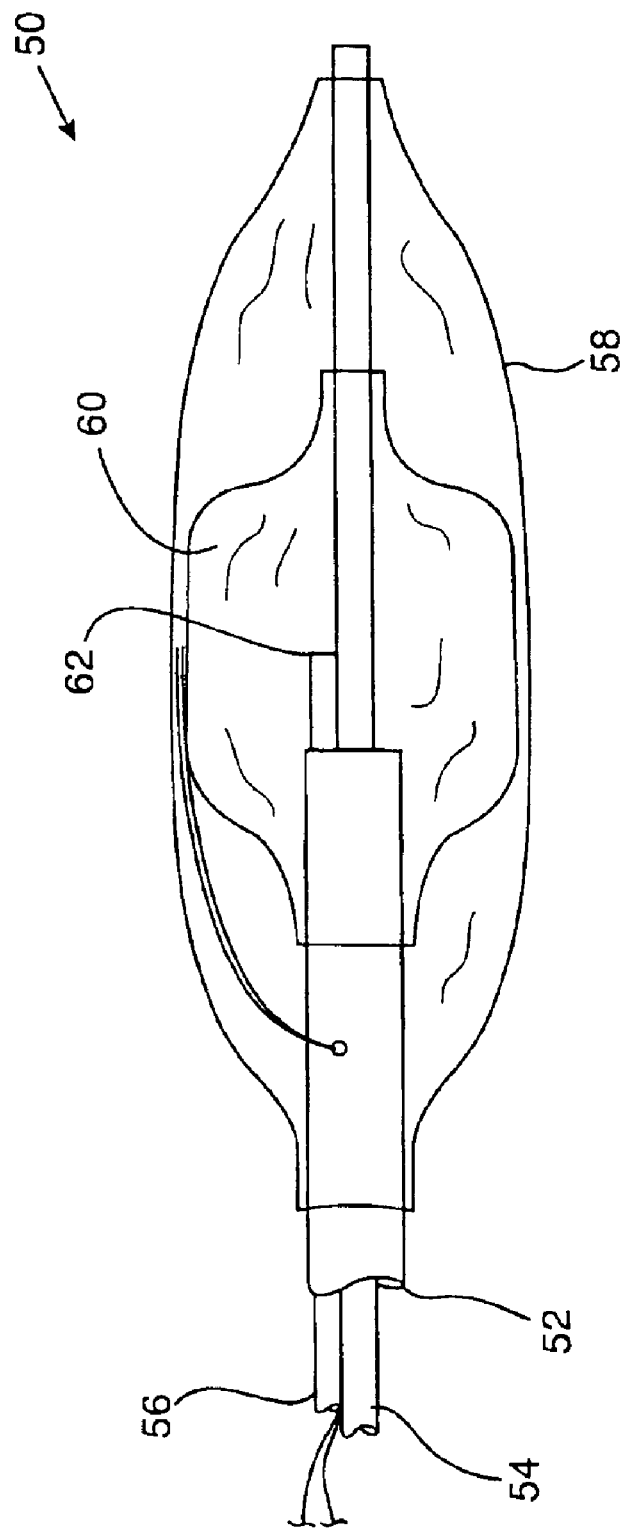
FIG. 5 illustrates the distal end of a cryosurgical catheter constructed in accordance with the principles of the present invention and having a nested containment bladder within a balloon structure.

Referring now to FIG. 5, an alternative balloon assembly 50 will be described. The balloon assembly 50 is disposed at the distal end of a catheter body 52 comprising a shaft 54 and a cryogenic fluid delivery tube 56. A balloon 58 is secured to the distal end of the catheter body 52, generally as described above with respect to catheter 10. In contrast to catheter 10, however, balloon assembly 50 comprises a containment bladder 60 nested within the balloon 58. The containment bladder 50 may be a second balloon formed in a manner similar to balloon 58, except that it will be shorter and will have proximal and distal ends spaced axially inwardly from the proximal and distal ends of balloon 58. The bladder 60, however, may be disposed of different materials and have different properties. Generally, the containment bladder is intended to receive and contain the gaseous nitrogen after it is expanded across expansion orifice 62 into the interior thereof. By containing the expanded (cold) gaseous nitrogen within bladder 60, a more distinct temperature transition may be effected between the cold middle region of balloon 58 and the less cold distal and proximal regions thereof.

Optionally, the balloon 58 may be separately expanded with an insulating fluid to further sharpen the temperature transition between the containment bladder 60 and the remainder of balloon 58. Alternatively, the containment bladder 60 may include ports or porous regions which permit the gaseous nitrogen to pass from the interior of the bladder 60 into the interior of balloon 58 in a controlled manner to maintain the desired temperature transition.

Figure 6A:
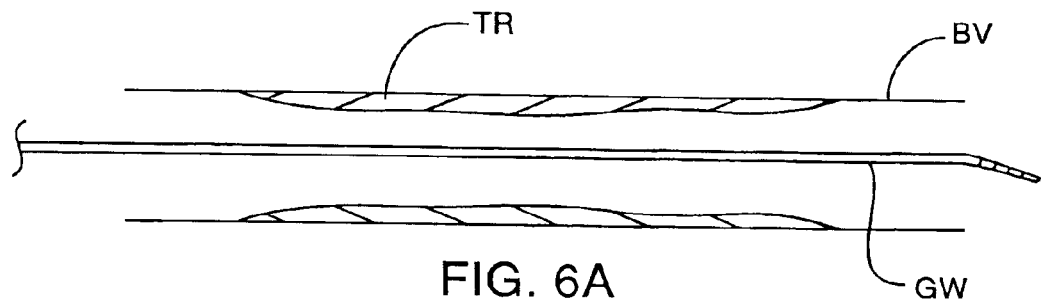
FIGS. 6A–6C illustrate use of the catheter of FIG. 1 in treating a target site within a patient's vasculature.
Figure 6B:
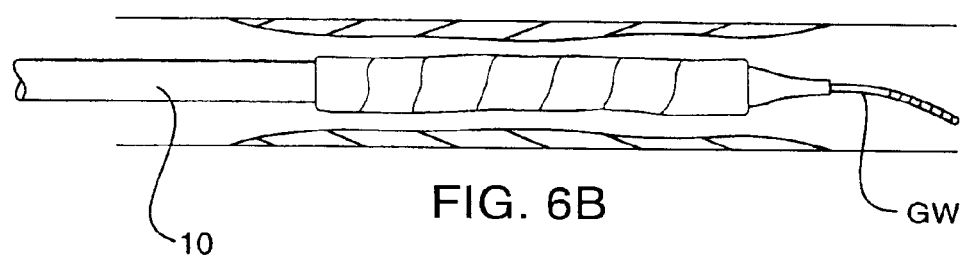
Figure 6C:
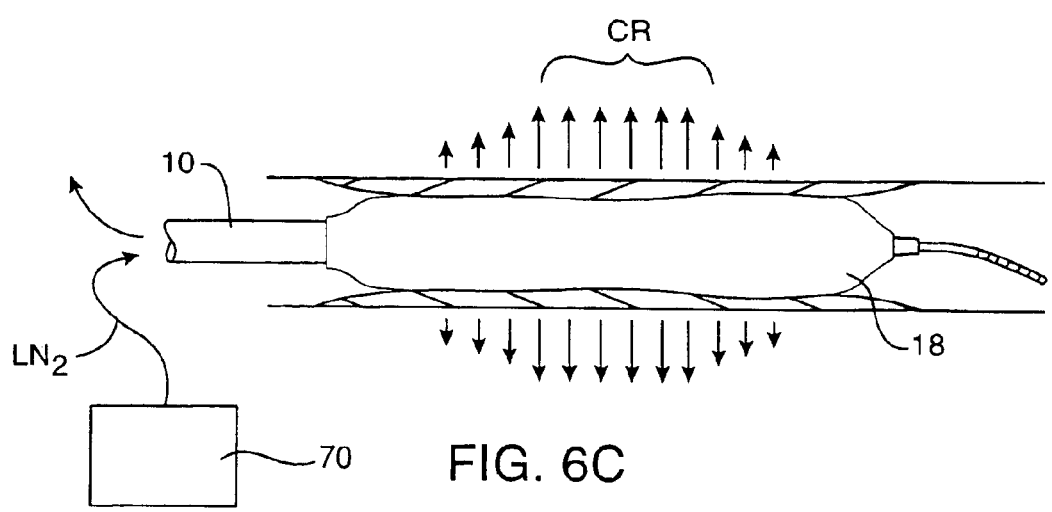

Referring now to FIGS. 6A–6C, use of catheter 10 for treating a target region TR within a blood vessel BV will be described. The target region will usually have been previously treated by balloon angioplasty or other primary conventional protocol for treating atherosclerotic disease. Such primary treatment will typically utilize an intravascular catheter, which catheter will have been removed leaving a guidewire GW in place, as illustrated in FIG. 6A. A catheter 10 is then introduced over the guidewire, as illustrated in FIG. 6B. Liquid nitrogen is introduced to the catheter 10 from a suitable source 70. The source may be a Dewar flask or other conventional source. In some instances, it will be possible to utilize recirculating refrigerated liquid nitrogen sources, such as those described in U.S. Pat. Nos. 5,644,502 and 5,617,739, the full disclosures of which have been previously incorporated herein by reference. The liquid nitrogen (LN2) is delivered to the catheter 10 and inflates balloon 18, as illustrated in FIG. 6C. Because of the temperature profile of the balloon, cooling of the inner wall of the blood vessel BV will be maximized over a central region CR and diminish in the proximal and distal directions from the central region, as illustrated qualitatively by the array of arrows in FIG. 6C. The treatment will be performed at the temperatures and for the times described thereabove in order to inhibit subsequent hyperplasia of the cells of the lining of the blood vessel. Advantageously, the cryogenic methods of the present invention will inhibit subsequent cell proliferation without inducing injury and thrombosis which can occur as a result of such injury.

Figure 7:
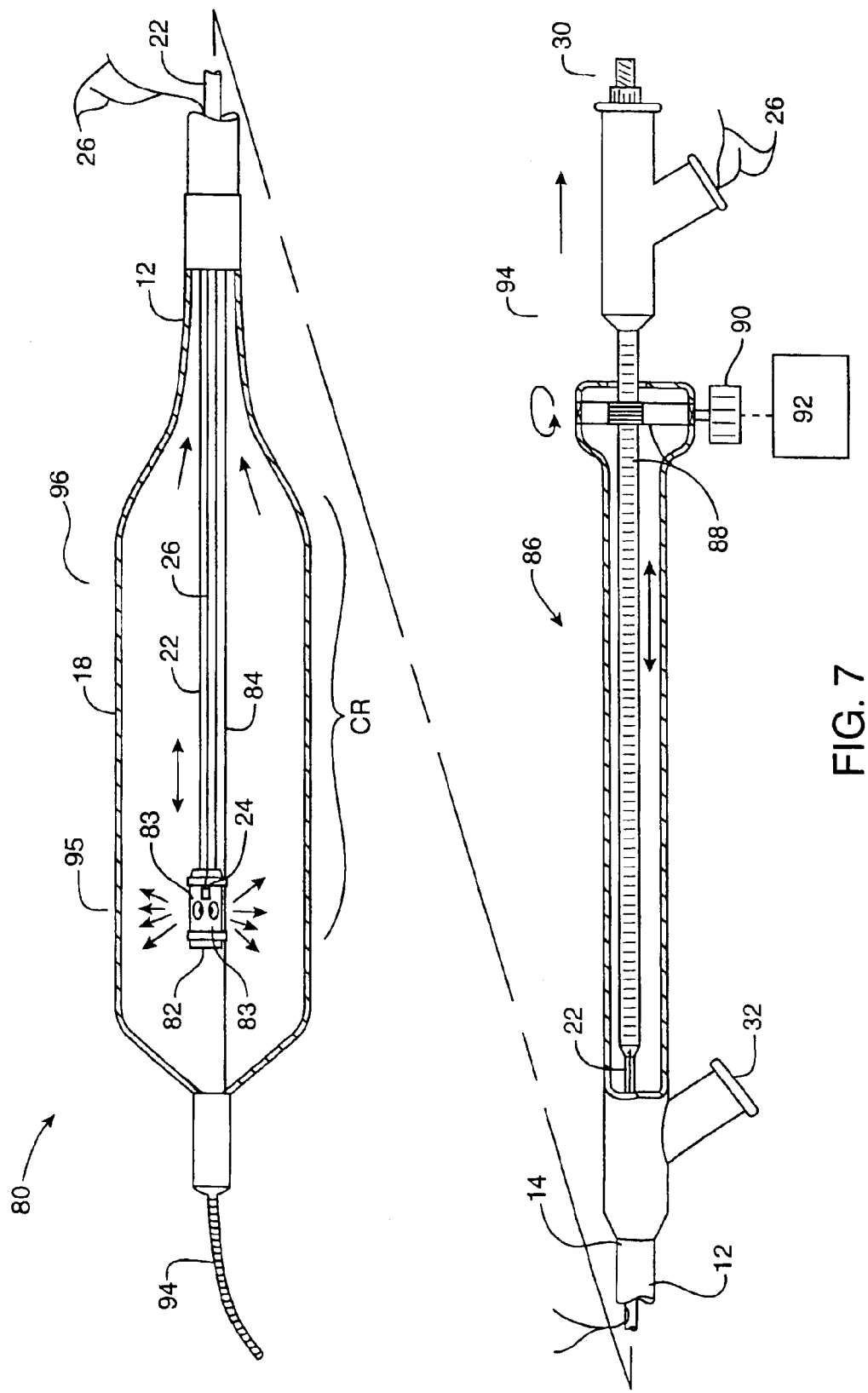
FIG. 7 is a partial cross-section of a cryosurgical catheter having a diffuser head with a plurality of radially oriented cryogenic fluid ports, in which the diffuser head can slide axially within the balloon to provide even cooling of elongate treatment sites.

A catheter 80 having a moveable port head or diffuser 82 is illustrated in FIG. 7. In this embodiment, cryogenic fluid ports 23 are separated circumferentially about diffuser 82, and are oriented radially so as to enhance the heat transfer between the expanding gas and the wall of balloon 18. In the embodiment illustrated here, four ports 83 are provided, and are separated circumferentially from each other by about 90°.

To enhance an axial length of a substantially evenly cooled central region CR, diffuser head 82 is slidably supported on a shaft or rail 84. Feed tube 22 is affixed to diffuser head 82 and is slidably disposed within catheter body 12. A proximal housing 86 at proximal end 14 of catheter 80 contains a rack and pinion mechanism 88 which controllably moves feed tube 22. By rotating control knob 90 (or automatically driving rack and pinion mechanism 88 with drive system 92), feed tube 22 and diffuser 82 can move from a first position 95 to a second position 96 without moving or deflating balloon 18. This allows a relatively small fluid flow to cool an elongate central region CR.

Inhibition of cell proliferation along elongate segments of vasculature, such as in the iliac or superior femoral arteries should benefit from cryosurgical treatment at repeatable temperatures and for repeatable times. To help prevent gaps between treatment regions and/or repeating treatments unintentionally, it would be advantageous to allow treatments of these elongate lumenal walls without moving or repositioning of the cryosurgical catheter. Hence, it is generally desirable to provide structures and methods which can uniformly apply radial cooling along these elongate endothelial surfaces.

Safety of endoluminal cryosurgical techniques is generally enhanced by minimizing the flow of the cooling fluid.

Low flow rates will generally reduce the release of gas into the body lumen in the unlikely event of a balloon rupture. Known balloon structures can withstand pressures of up to about 100 psi or more. Nonetheless, safety can be enhanced by limiting maximum balloon pressures to 100 psi or less, and preferably to less than 100. Lower balloon pressures not only reduce the amount of gas released in the event of a rupture, they also help decrease the possibility of such a balloon rupture occurring. Given a constant cooling fluid pressure at port 83, lower pressures within balloon 18 will also produce a lower balloon wall temperature. In other words, cryogenic cooling is generally enhanced by minimizing the pressure within the balloon.

As there is a limited cross-sectional area available for exhausting the expelled gases, pressure within the balloon is most easily minimized by decreasing the speed (and pressure head loss) of exhaust gases flowing proximally through catheter body 12 to exhaust port 32. Drawing a vacuum at exhaust port 32 can encourage the flow of gases proximally and reduce balloon pressure to some extent, but this will provide limited benefits when gas velocity and pressure drops are high within the catheter body. Hence, it is beneficial to make efficient use of a relatively small cryogenic fluid flow. By moving diffuser 82 axially within balloon 18, an elongate region of the vessel wall can be treated sequentially with a modest cryogenic fluid supply and a low balloon pressure. As the amount of time the tissues are to be cooled is quite short, the total procedure time remains very reasonable.

The use of moveable diffuser head 82 also allows the surgeon to selectively treat tissues in a highly controlled manner. For example, when balloon 18 extends across a branch artery, the surgeon has the option of treating the vessel proximally and distally of the branch and shutting off the gas flow when the diffuser is aligned with the branch so as to avoid freezing blood within the branch opening. Additionally, by coupling automated drive system 92 to the actuation mechanism, a wide variety of treatment cycles and times may be controllably and repeatably effected.

Balloon 18 of moveable diffuser catheter 80 may be quite elongate, the balloon typically having a length in a range from about 1 to about 10 cm. In the exemplary embodiment, the balloon has a length of about 10 cm so that proximal housing 86 and/or actuation mechanism 88 has a stroke length of about 8 cm. To enhance heat flow through balloon 18, a heat transfer enhancing material may be included in the polymer of the balloon wall. For example, the addition of between about 1 and 10% boron nitride in a polyethylene or other balloon polymer can significantly improve heat transfer of the entire system. Surprisingly, a significant temperature differential may be found between an inner and outer surface of the balloon during cooling. Hence, improving the thermal conductivity of the balloon material may provide significant benefits.

In the embodiment of FIG. 7, a fixed guidewire 94 extends distally from the balloon to help when advancing catheter 80 within the vasculature. Fixed guidewire 94 and the distal end of balloon 18 are affixed to an axial support or rail 84 which structurally supports the distal end of the catheter when the balloon is not inflated. Rail 84 here comprises a stainless steel wire with a diameter of 0.008 inches, but may alternatively comprise a wide variety of shaft structures, optionally including one or more lumens for a moveable guidewire or the like.

Diffuser 82 includes four radially oriented ports, each having a diameter of about 0.0025 inches. These openings are in fluid communication with a central passage, which in turn is supplied by feed tube 22. Diffuser head 82 may have an outer diameter of about 0.032 inches, and may comprise any of a variety of alternative polymers or metals. Diffuser 82 is affixed to feed tube 22 by adhesion bonding, heat welding, fasteners, or the like. In the exemplary embodiment, diffuser 82 comprises polyimide. Feed tube 22 may also be formed from a polyimide tube, and will preferably be coated with a PTFE such as Teflon™ to avoid friction when the feed tube reciprocates within the catheter body. Diffuser head 82 is shown affixed to rail 84 using bands which encircle the diffuser and define a channel through which rail 84 passes. Clearly, a wide variety of alternative support arrangements are possible, including a concentric support shaft or tube, a cantilevered feed tube, or the like. As described above, thermocouple 24 or some alternative temperature sensor sends a signal proximally via wire 26 to indicate the temperature within the balloon.

In use, moveable diffuser balloon catheter 80 will be introduced into a blood vessel while balloon 18 is in an uninflated, small profile configuration. Balloon 18 will be maneuvered to the treatment site using fixed guidewire 94. Feed tube 22 will be positioned so that diffuser 82 is located at first position 95, and cryogenic fluid will be advanced through feed tube 22 to the diffuser. This gas will inflate balloon 18, and will also cool the interior surface of the balloon and blood vessel as described above. Control knob 90 will be rotated so that diffuser 82 moves axially toward position 96. As the cooling fluid exits the diffuser, the endothelial tissue engaging central region CR is cryogenically cooled.

Cryogenic cooling fluid may optionally pass through a Joule-Thompson orifice adjacent port 83 to effect cooling. In other embodiments, at least a portion of the cryogenic cooling fluid may exit port 83 into the balloon as a liquid. The liquid will vaporize within the balloon, and the enthalpy of vaporization can help cool the surrounding vessel wall. The liquid may coat at least a portion of the balloon wall so as to enhance even cooling over at least a portion of the vessel wall. Hence, ports 83 may have a total cross section which is smaller than a cross section of the fluid supply lumen, or which is at least as large as the cross section of the fluid supply lumen.

By controlling the rate of movement of diffuser 82 via control knob 90, the amount of cooling fluid injected via feed tube 22, and the pressure at exhaust port 32, the surgeon can control the cooling rate of the tissue, the temperature of the tissue, and optionally, the number of cooling cycles the tissue is subjected to while the catheter is in a single location. As described above, the ends of the diffuser stroke first and second positions 95, 96 may be separated from the axial ends of balloon 18 so as to limit any cooling of fluids within the vessel.

Figure 8:
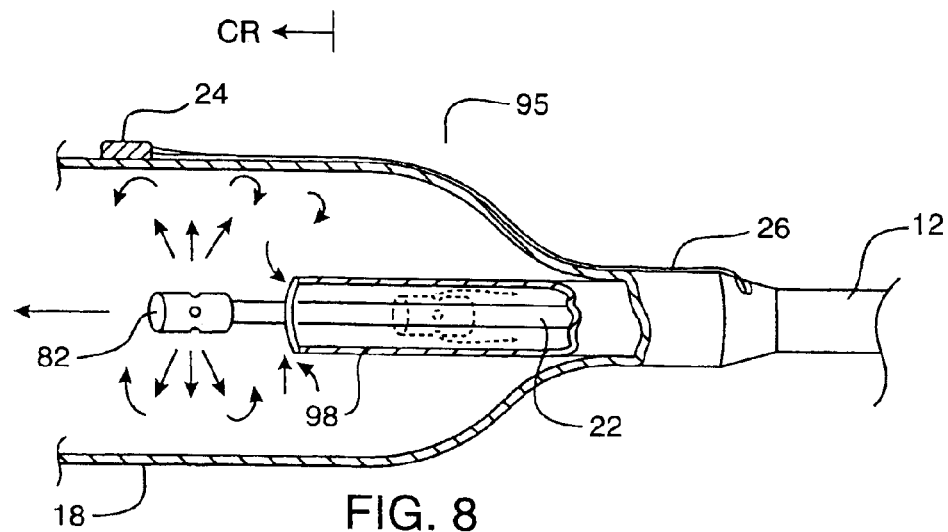
FIG. 8 is a partial cross-sectional view of a cryosurgical catheter having a moveable diffuser head which can be drawn proximally into a housing within the balloon so as to avoid transients upon initiation of the cooling fluid flow.

As can be understood with reference to FIG. 8, it will be desirable to control the initial rate of cooling when cryogenic fluid first starts to exit diffuser 82. As the balloon inflates and the diffuser structure cools, significant thermal transients will occur before the desired steady state cryogenic cooling begins. To avoid unpredictable or excessively slow cooling rates, diffuser 82 may initially be parked within a housing 98 inside balloon 18. Housing 98 may be formed by extending a tube from catheter body 12 into balloon 18, the housing optionally comprising an extension of the catheter body material.

An additional benefit of housing 98 may be understood with reference to FIGS. 7, 8, and 4. As cooling gas flows from diffuser 82 into balloon 18, the expelled gases are exhausted proximally from the balloon into catheter body 12. Although the gases will warm as they travel proximally, the gas flow will be accelerating from their relatively large cross-sectional diameter of the balloon into the catheter body. This may actually enhance cooling adjacent the proximal end of the balloon, and could freeze blood proximally of the balloon.

To avoid this enhanced proximal cooling, housing 98 admits gases from a central location along central region CR. The gases surrounding housing 98 within balloon 18 are allowed to stagnate near the proximal end of the balloon, thereby limiting axial cooling at that location.

As described above, there may be a significant temperature differential between the inner surface and the outer surface of the balloon wall. To more accurately and repeatably monitor cryosurgical therapy, a temperature sensor 24 is mounted on the outer surface of the balloon to measure the temperature of the tissue at the target site, the tissue balloon interface, and/or the balloon outer surface temperature.

Figure 9:
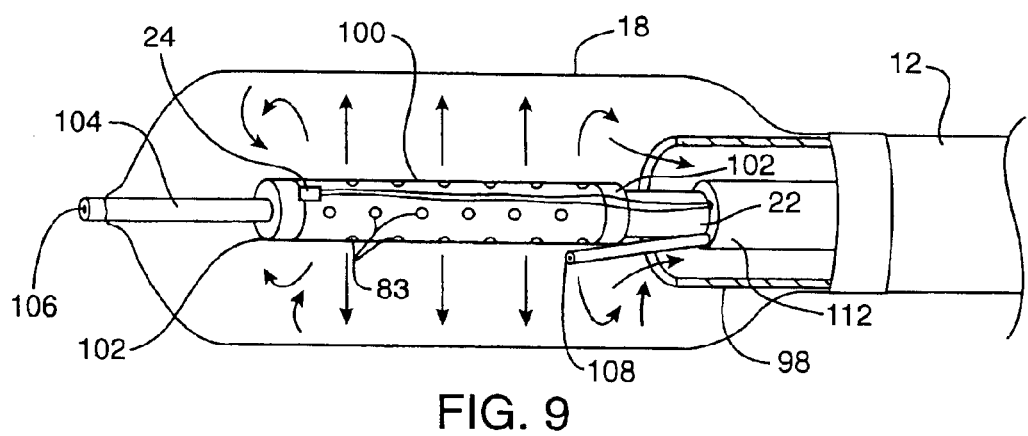
FIG. 9 schematically illustrates an alternative fixed porous diffuser defining an axial and circumferential array of orifices.

Referring now to FIG. 9, a fixed diffuser 100 includes an array of ports 83 which are distributed both axially and circumferentially around the diffuser. As ports 83 are radially oriented, diffuser 100 will achieve the desired cooling of the surrounding tissue with relatively low balloon pressures and low cooling fluid flow rates. As the cryogenic liquid or gas-liquid combination is directed perpendicularly against the wall of balloon 18, the heat transfer coefficient between the gas and the balloon wall is quite high. This helps to reduce temperature of the balloon and provides greater heat extraction for a given flow rate of coolant into the balloon. Additionally, as ports 83 are distributed both circumferentially and axially along the balloon, diffuser 100 will distribute the cooling more uniformly over the surface of the balloon so as to produce a uniform antiproliferative response.

Diffuser 100 will generally comprise a tubular structure with radially oriented openings. An exemplary tubular structure may comprise a polyimide tube having an inner diameter of about 0.032 inches and a wall thickness of 0.001 inch. Each port will again define a diameter of about 0.0025 inches. There will typically be between about 6 and 600 orifices in diffuser 100. In the exemplary embodiment, four axial rows of orifices are separated by about 90° from each other. The rows are axially staggered so that the orifices in a single row have centerline separations of about 4 mm, while the orifices of adjacent rows are separated by about 2 mm. The overall length of the porous diffuser tube is about 2 cm.

A central shaft 104 having a guidewire lumen 106 is bonded concentrically to diffuser 100 using adhesive or the like at the distal end of the diffuser, and optionally also at the proximal end of the diffuser. High contrast markers 102 may be provided to enhance an image of the catheter so as to facilitate positioning of balloon 18 fluroscopically, sonographically, or under any other alternative image modality (with appropriate contrast structures). The distal marker may optionally be formed by winding a gold or platinum wire around the central shaft and bonding the gold wire to the distal end of the diffuser tube. The proximal marker may similarly be formed by winding and bonding a gold or platinum wire, the proximal marker optionally being disposed over the diffuser tube so that the cryogenic cooling fluid may be introduced through the annular space between the diffuser tube and the central shaft proximally of the balloon. Central shaft 104 will typically comprise a polyimide tube, but may alternatively comprise any of a wide variety of materials.

The coaxial arrangement between diffuser 100 and central shaft 104 (with an annular cooling fluid flow path between the tube of the diffuser and the central shaft) promotes circumferentially symmetric distribution of the cryogenic cooling fluid against the balloon wall, which in turn provides a more circumferentially even temperature distribution. As generally described above, uniform temperature distributions, both axially and circumferentially, within central region CR (see FIG. 4) help ensure that the beneficial inhibition of cell proliferation is provided throughout a significant portion of the tissue engaged by balloon 18. To limit cooling of tissues or fluids disposed axially of the balloon, distal and proximal stagnant regions within the balloon flow profile are created by the shape and configuration of diffuser 100, balloon 18, and by the presence of housing 98 within the proximal end of the balloon, as described above. Even though no moveable diffuser will be drawn into housing 98, this structure still helps to avoid the accelerating flow of gases along the proximally tapering balloon wall.

To accurately control the cooling process, it is beneficial to monitor pressure within the balloon. Toward that end, a balloon pressure port 108 transmits pressure proximally via a pressure monitoring lumen 110, as can be understood with reference to FIGS. 9 and 10. Accuracy of such pressure monitoring can be enhanced by minimizing the flow of fluid proximally within the pressure monitoring lumen. Alternatively, a pressure transducer may be mounted within the balloon with wires sending a pressure signal proximally. Within the elongate catheter body 12, lumens for the cryogenic feed tube 22, pressure monitoring port 108, guidewire and the like may be contained within an insulated jacket 112. As balloon 18 may elongate when inflated, and as the distal end of diffuser is affixed to the distal end of the balloon by core shaft 104, it may be beneficial to allow jacket 112 to slide axially within catheter body 12 to avoid axial bending of the balloon and the resulting radially uneven cooling. In alternative embodiments, a cryogenic feed tube may simply extend distally into an annular space between a central shaft and a jacket formed as a continuous proximal extension of the diffuser tube, with any proximal leakage of the cooling fluid within the jacket optionally being exhausted into the catheter body and removed via the exhaust lumen.

Figure 10:
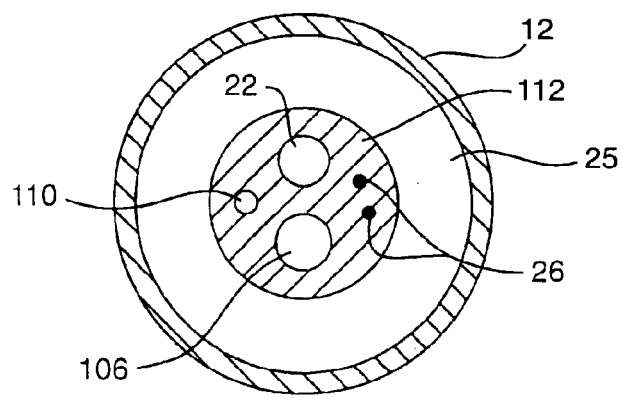
FIG. 10 illustrates a cross-section of the catheter of FIG. 9.
Figure 11:
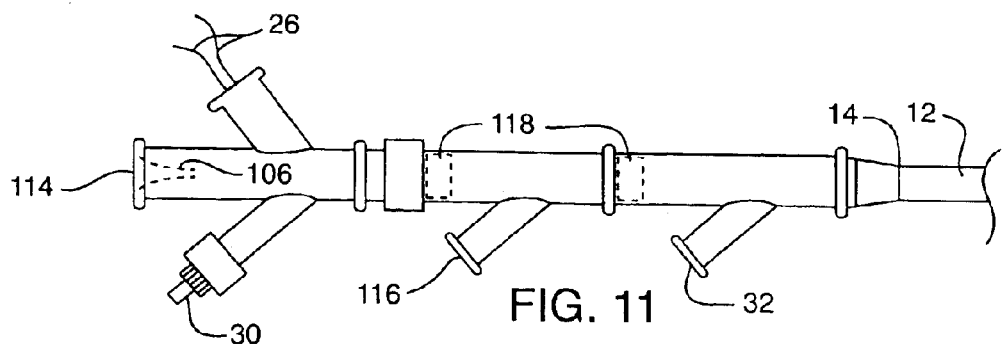
FIG. 11 illustrates a proximal end of the catheter of FIG. 9.

Referring now to FIG. 11, a proximal end of the fixed diffuser catheter illustrated in FIGS. 9 and 10 include many of the coupling structures described above regarding FIGS. 1 and 7. Guidewire port 114 provides proximal access to guidewire lumen 106, while a pressure monitoring connector 116 is in fluid communication with the interior of balloon 18 via monitoring lumen 110. Where balloon pressures are acceptable, cryogenic cooling may optionally be controlled using an orifice disposed at exhaust port 32. This proximal structure can be assembled from commercial available components using potting adhesive 118 in a generally conventional manner.

Figure 12:
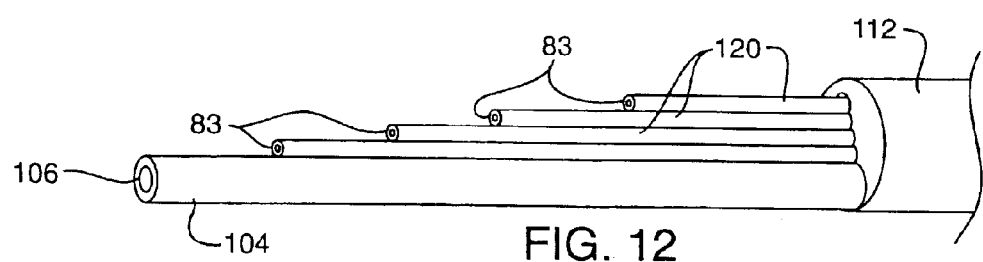
FIG. 12 illustrates an alternative fixed diffuser structure having an array of axially separated cryogenic fluid ports.
Figure 13:
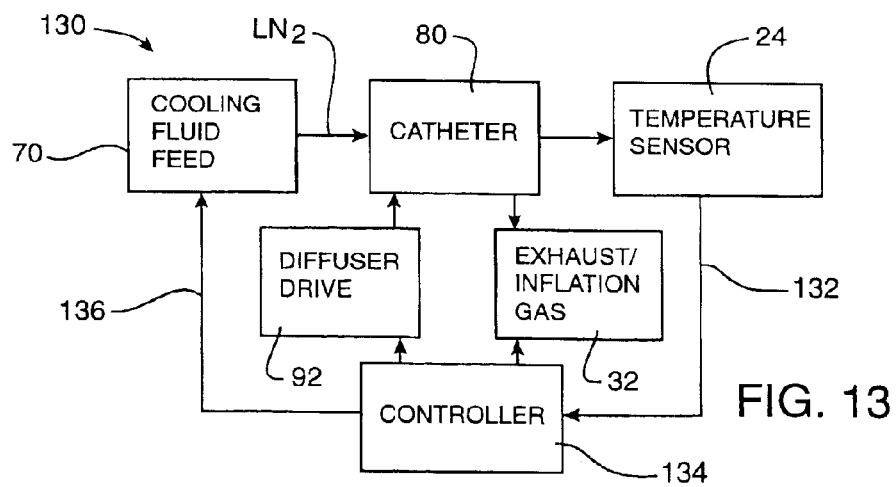
FIG. 13 is a functional block diagram illustrating the operation of the catheter of FIG. 7, including an optional feedback control loop.

Referring now to FIG. 12, still further alternative multiple orifice diffuser structures are possible. In this embodiment (illustrated here without balloon 18) a series of ports 83 are distributed axially so as to distributed the cooling axially within an elongate target region, as generally described above. In this embodiment, a series of individual gas feed tubes 120 supply the cryogenic cooling fluid to the ports, with each port optionally having an opening which has the same area as the lumen of the associated gas feed tube. Such individual feed tubes may comprise polyimide tubes having an inner diameter of about 0.005 inches. In some embodiments, axial distribution of cooling may be controlled by varying the amount of fluid expelled from each port, by varying the interorifice spacing (axially and/or circumferentially), by locally varying the heat transfer coefficient or cooling fluid pattern, or the like.

It will generally be beneficial to make use of catheter 80 as one component of an integrated cryosurgical endoluminal therapy system 130. As the actual tissue cooling may vary with pressures within the balloon, cooling fluid flow rates, and the like, and as these parameters may vary when catheter body 12 is bent in following the vasculature system, the efficacy of the cryosurgical therapy may be enhanced by adjusting the treatment based on measured characteristics of the cooling process, for example, based on temperatures measured by one or more temperature sensors 24. Hence, electrical temperature signals 132 from temperature sensors 24 may be directed to a controller 134 for use in a feedback control system. Preferably, controller 134 processes the temperature signals to generate cooling fluid feed signals 136 indicating the pressure or volume of cryogenic fluid to be injected into the catheter. Controller 134 will preferably also provide electrical signals which direct diffuser drive 92 to mechanically reposition diffuser 82, and will often provide signals varying the pressure (or vacuum) at exhaust port 32. These signals may be used not only to vary the cooling cycle, but can also be used to control the inflation and/or deflation of the balloon, preferably based at least in part on a pressure monitored from within the balloon.

To inhibit cell proliferation and/or remodeling, controller 134 will generally initiate, monitor, and control cooling of the tissue. Cryogenic system 130 will often be used to effect a cooling rate of the tissue in a range from about 2 to about 30° C. per second. In an exemplary cell proliferation inhibition therapy, the system will maintain the tissue at a temperature in a range from about 0 to about −80° C., preferably at a temperature in a range from about −10 to about −40° C., for a time between about 1 and about 60 seconds. The efficacy of the therapy may be enhanced by repeatedly cooling the tissue to these temperatures for between 1 and 5 cooling cycles, typically repeating the cooling cycles at the rate of 1 every 60 seconds. To provide this cooling, cryogenic liquids or liquid/gas mixtures comprising carbon dioxide, nitrous oxide, or the like may flow through the balloon at a rate in a range from about 100 to about 800 mg/sec. Such cooling may inhibit cell proliferation via processes which are sometimes referred to as apoptosis and/or programmed cell growth.

Figure 14:
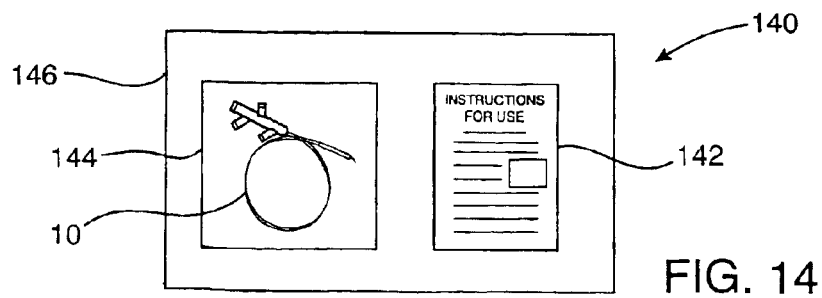
FIG. 14 schematically illustrates a kit including a balloon catheter and instructions for its use according to the methods described herein.

A kit 140 including balloon catheter 10 and instructions for its use 142 is illustrated in FIG. 14. Catheter 10 may be replaced by any of the balloon catheter structures described above, while instructions for use 142 may describe any of the associated method steps set forth above for inhibition of cell proliferation. Instructions for use 142 will often be printed, optionally appearing at least in part on a sterile package 144 for balloon catheter 10. In alternative embodiments, instructions for use 142 may comprise a machine readable code, digital or analog data graphically illustrating or demonstrating the use of balloon catheter 10 to inhibit hyperplasia, or the like. Still further alternatives are possible, including printing of the instructions for use on packaging 146 of kit 140, and the like.

While the above is a complete description of the preferred embodiments of the invention, various alternatives, modifications, and equivalents may be used. For example, one or more radial orifices might move both circumferentially and axially within the balloon, optionally along a helical path, to provide cylindrically even cooling. Therefore, the above description should not be taken as limiting the scope of the invention which is defined by the appended claims.

What is claimed is:

1. A method for treating a blood vessel having a vessel wall, the method comprising:

introducing a catheter into the blood vessel;

expanding a balloon of the catheter near a target site within the vessel wall, the balloon having a balloon wall;

cooling the vessel wall with the balloon by coating at least a portion of an inner surface of the balloon wall with a liquid so that the liquid coating vaporizes, the coating engaging the balloon wall within the balloon.

2. The method of claim 1, further comprising;

expanding the liquid at a first location within the balloon; and expanding the liquid at a second location within the balloon to cryogenically evenly cool the engaged vessel wall, the second location being circumferentially separated from the first location.

3. The method of claim 2, further comprising moving a diffuser head between the first location and the second location.

4. The method of claim 3, wherein a housing separates the balloon and the vessel wall when the orifice head is at the first location, wherein fluid expansion is initiated at the first location, and wherein the moving step moves ports of the diffuser head from within the housing after a reduction in thermal of the gas expansion.

5. The method of claim 2, wherein fluid expansion occurs simultaneously at the first and second locations, the balloon being axially elongate, the first and second locations being separated axially.

6. The method of claim 2, wherein the fluid expansion occurs simultaneously at the first and second locations so that the fluid flows radially toward the vessel wall.

7. The method of claim 2, wherein the first and second expansion steps comprise vaporization of at least a portion of the fluid from a liquid to a gas so that the enthalpy of vaporization cools the at least a portion of the engaged vessel wall.

8. A method for treating a blood vessel having a vessel wall, the method comprising:

introducing a catheter into the blood vessel;

expanding a balloon of the catheter near a target site within the vessel wall, the balloon having a balloon wall;

cooling the vessel wall with the balloon by coating at least a portion of an inner surface of the balloon wall with a liquid, the liquid vaporizing within the balloon.

9. The method of claim 8, wherein the at least a portion of the inner surface of the balloon wall is coated by introducing a cryogenic cooling fluid through a port into balloon so that at least a portion of the cryogenic cooling fluid exits the port as the liquid.

10. The method of claim 9, wherein the liquid coats the at least a portion of the inner surface of the balloon wall so as to enhance even cooling over at least a portion of the vessel wall engaged by the balloon.

11. The method of claim 10, wherein the liquid coating the balloon wall vaporizes while the coating engaged the balloon wall within the balloon.

* * * * *